(12) United States Patent
Tanzer (10) Patent No.: US 7,137,971 B2
(45) Date of Patent: Nov. 21, 2006

(54) INCONTINENCE GARMENT HAVING PLEATED EXTENSIBLE LIQUID RETENTION LAYER

(75) Inventor: Richard Warren Tanzer, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 392 days.

(21) Appl. No.: 10/101,509

(22) Filed: Mar. 19, 2002

(65) Prior Publication Data

US 2003/0014031 A1    Jan. 16, 2003

Related U.S. Application Data

(63) Continuation-in-part of application No. 09/385,132, filed on Aug. 27, 1999, now abandoned.

(51) Int. Cl.
*A61F 13/15* (2006.01)
(52) U.S. Cl. .............. 604/385.201; 604/385.01; 604/385.101; 604/380; 604/379
(58) Field of Classification Search ........... 604/385.14, 604/385.16, 385.201, 385.22, 385.28, 385.01, 604/385.101, 380, 379
See application file for complete search history.

(56) References Cited

U.S. PATENT DOCUMENTS

| 810,130 | A | * | 1/1906 | Green ............... 604/378 |
|---|---|---|---|---|
| 3,338,992 | A | | 8/1967 | Kinney ............... 264/24 |
| 3,341,394 | A | | 9/1967 | Kinney ............... 161/72 |
| 3,469,286 | A | * | 9/1969 | Crockford ............ 28/120 |
| 3,481,337 | A | * | 12/1969 | Ruffo ................ 604/366 |
| 3,485,706 | A | | 12/1969 | Evans ................ 161/72 |
| 3,502,538 | A | | 3/1970 | Petersen ............. 161/150 |
| 3,502,763 | A | | 3/1970 | Hartmann ............ 264/210 |
| 3,525,337 | A | * | 8/1970 | Simons et al. ........ 604/366 |
| 3,542,615 | A | | 11/1970 | Dobo et al. .......... 156/181 |
| 3,561,446 | A | | 2/1971 | Jones, Sr. ........... 128/287 |
| 3,653,382 | A | | 4/1972 | Easley et al. ........ 128/284 |
| 3,692,618 | A | | 9/1972 | Dorschner et al. ...... 161/72 |
| 3,802,817 | A | | 4/1974 | Matsuki et al. ........ 425/66 |
| 3,849,241 | A | | 11/1974 | Butin et al. .......... 161/169 |
| 3,901,236 | A | | 8/1975 | Assarsson et al. ..... 128/284 |
| 4,076,663 | A | | 2/1978 | Masuda et al. ..... 260/17.4 GC |
| 4,100,324 | A | | 7/1978 | Anderson et al. ...... 428/288 |
| 4,259,387 | A | | 3/1981 | Mesek ................ 428/167 |
| 4,286,082 | A | | 8/1981 | Tsubakimoto et al. .... 526/240 |
| 4,340,563 | A | | 7/1982 | Appel et al. ......... 264/518 |
| 4,576,853 | A | * | 3/1986 | Vaughn et al. ........ 428/181 |
| 4,655,760 | A | | 4/1987 | Morman et al. ....... 604/385 |
| 4,818,464 | A | | 4/1989 | Lau .................. 264/510 |
| 4,847,134 | A | | 7/1989 | Fahrenkrug et al. .... 428/138 |
| 5,248,309 | A | * | 9/1993 | Serbiak et al. ....... 604/368 |
| 5,272,236 | A | | 12/1993 | Lai et al. ........... 526/348.5 |

(Continued)

FOREIGN PATENT DOCUMENTS

WO        96/05786        2/1996

(Continued)

*Primary Examiner*—Jacqueline F. Stephens
(74) *Attorney, Agent, or Firm*—Pauley Petersen & Erickson (57) ABSTRACT

An primary liquid retention layer suitable for use in an incontinence garment includes a plurality of pleats defined by fold lines in at least one region of the composite. The fold lines are oriented in a first direction. The primary liquid retention layer is stretchable in a second direction perpendicular to the fold lines, between a first position where the pleats are substantially folded and a second position where the pleats are substantially unfolded or extended due to liquid loading, while the primary liquid retention layer remains substantially in the plane of the garment so as to not distort the wetted appearance of the garment.

32 Claims, 3 Drawing Sheets

U.S. PATENT DOCUMENTS

| | | | |
|---|---|---|---|
| 5,322,728 A | 6/1994 | Davey et al. | 428/296 |
| 5,364,382 A | 11/1994 | Latimer et al. | 604/378 |
| 5,366,452 A | 11/1994 | Widlund et al. | 604/385.2 |
| 5,376,198 A | 12/1994 | Fahrenkrug et al. | 156/164 |
| 5,389,095 A | 2/1995 | Suzuki et al. | 604/385.2 |
| 5,411,497 A | 5/1995 | Tanzer et al. | 604/368 |
| 5,425,725 A | 6/1995 | Tanzer et al. | 604/368 |
| 5,433,715 A | 7/1995 | Tanzer et al. | 604/368 |
| 5,451,219 A | 9/1995 | Suzuki et al. | 604/385.2 |
| H001511 H * | 12/1995 | Chappell et al. | 604/383 |
| 5,509,915 A | 4/1996 | Hanson et al. | 604/378 |
| 5,520,673 A | 5/1996 | Yarbrough et al. | 604/378 |
| 5,560,878 A | 10/1996 | Dragoo et al. | 264/115 |
| 5,562,650 A * | 10/1996 | Everett et al. | 604/378 |
| 5,571,619 A | 11/1996 | McAlpin et al. | 428/364 |
| 5,593,399 A | 1/1997 | Tanzer et al. | 604/368 |
| 5,601,542 A | 2/1997 | Melius et al. | 604/368 |
| 5,645,542 A | 7/1997 | Anjur et al. | 604/368 |
| 5,662,634 A | 9/1997 | Yamamoto et al. | 604/378 |
| 5,683,374 A | 11/1997 | Yamamoto et al. | 604/385.2 |
| 5,702,381 A | 12/1997 | Cottenden | 604/385.1 |
| 5,766,213 A | 6/1998 | Hackman et al. | 604/385.1 |
| 5,824,004 A | 10/1998 | Osborn, III et al. | 604/385.2 |
| 5,883,028 A | 3/1999 | Morman et al. | 442/394 |
| 5,895,379 A | 4/1999 | Litchholt et al. | 604/378 |
| 6,149,638 A * | 11/2000 | Vogt et al. | 604/385.01 |

FOREIGN PATENT DOCUMENTS

| | | |
|---|---|---|
| WO | 96/16624 | 6/1996 |
| WO | WO 97/05769 * | 2/1997 |

* cited by examiner

INCONTINENCE GARMENT HAVING PLEATED EXTENSIBLE LIQUID RETENTION LAYER

CROSS REFERENCE TO RELATED APPLICATION

The present application is a Continuation-In-Part of application Ser. No.: 09/385,132,filed on 27 Aug. 1999 now abandoned.

BACKGROUND OF THE INVENTION

This invention is directed to an incontinence garment having a pleated, extensible, absorbent, primary liquid retention layer. The pleated liquid retention layer is selectively stretchable in a direction perpendicular to the pleats, may have elastic recovery properties, and is economical to produce, while providing sufficient aesthetics and capacity to serve as the liquid retention layer of an incontinence garment.

It is known to make incontinence garments, such as disposable diapers and pant-like absorbent garments, using stretchable materials. Some incontinence garments are rendered stretchable by placing elastic bands in the waist and leg regions, and otherwise employing inelastic construction materials. In some instances, incontinence garments have employed elastic or otherwise stretchable materials in constructing the primary layers. This approach has been limited because most incontinence garments include, at minimum, a liquid-permeable top layer, an absorbent core composite, and a substantially liquid impermeable outer cover material. The use of an elastic or stretchable material in one or more layers will not render the incontinence garment stretchable unless each and every layer can be made from a similarly stretchable material. Often, the absorbent composite in the core is the least stretchable of the layers, and tears when the top layer and outer cover materials can be stretched to a greater degree.

Stretchable incontinence garments are disclosed, for instance in U.S. Pat. No. 5,560,878 issued to Dragoo et al., and in U.S. Pat. No. 5,645,542, issued to Anjur et al. In the disclosed articles, all of the layers are stretchable. Other stretchable incontinence garments are disclosed in U.S. Pat. Nos. 4,847,134 and 5,376,198, both issued to Fahrenkrug et al. In these articles, some of the layers are more stretchable than others. The less stretchable outer layers form rugosities upon relaxation.

One challenge in making stretchable incontinence garments is the provision of a primary liquid retention layer of economical fibrous material which is stretchable and yet capable of absorption and retention of high volumes of liquid needed for an incontinence garment application. Some of the most advanced absorbent composites, having the highest absorbencies and liquid retention, include relatively high percentages of absorbent and superabsorbent materials contained in a relatively lower percentage of nonwoven web filament matrix. Efforts to render these composites stretchable have focused on forming the nonwoven web filament matrix from elastic polymers. However, because the matrix polymer is often a minor component of these high percentage composites, the elastic matrix polymer has limited influence on the elasticity of the entire composite. Additionally, the matrix filaments can separate or tear during stretching.

Thus, there is a need or desire for primary liquid retention layers having high loadings of absorbent and superabsorbent materials, which have controlled stretchability in desired directions. Further, it is highly desirable that the primary liquid retention layer be easily and economically made while providing sufficient liquid absorption and retention capacity to collect and retain the higher volumes of liquid associated with incontinent voiding of urine or feces. It is further desirable that the primary liquid retention layer provide good aesthetics such that the wetted incontinence garment look as similar to the dry incontinence garment as possible. Such aesthetic considerations would be helped by a primary liquid retention layer which is expandible in the plane of the primary liquid retention layer rather than bulging or expanding out-of-plane, and which further may have some elastic capacity to retain a desirable shape under a liquid loading.

Some pleated absorbent structures are known. U.S. Pat. No. 5,702,381 to Cottenden teaches a light-duty male incontinence device having pleats therein designed to form a cup shaped device for surrounding male genitalia, presumably prior to urine loading. It is not believed Cottenden teaches expansion of its pleats upon wetting, nor teaches a sufficient capacity of liquid retention to serve as a true diaper or adult incontinence garment. U.S. Pat. No. 5,824,004 to Osborn III, et al. teaches a pleated absorbent core of cellulosic foam suitable for feminine hygiene absorbent products designed to distort out of plane under liquid loading. Also, the use of cellulosic foams in incontinence garments, with their demand for greater fluid volume retention, would require greater use of the sponge-like cellulosic foam material. Unfortunately, cellulosic foams are generally more expensive to produce than fibrous nonwovens. Also, cellulosic foams are not believed to provide a suitable elasticity of the liquid retention layer and are generally considered harder to work with in garment manufacturing than fibrous nonwovens.

SUMMARY OF THE INVENTION

The present invention is directed to incontinence garments having a highly absorbent primary liquid retention layer based upon a pleated fibrous nonwoven web composite which addresses the foregoing concerns and serves as the primary liquid absorption and retention layer for the garment. The primary liquid retention layer may include a combination of nonwoven matrix fibers, superabsorbent particles or fibers, and, optionally, absorbent fibers, e.g., cellulosic fibers, so as to be easily pleated and extensible in the plane of the garment while providing a high volume of absorption and liquid retention to the incontinence garment. The primary liquid retention layer does not generally include any significant amounts of cellulosic foam/sponge material. In one embodiment, the superabsorbent particles or fibers, and optional absorbent fibers, are contained within a nonwoven web, between the matrix fibers. In another embodiment, the superabsorbent polymers or fibers, and optional absorbent fibers, may be contained between two nonwoven webs of fibers.

In accordance with the invention, the primary liquid retention layer is pleated by forming folds at regular intervals. The folds defining the pleats are oriented perpendicular to the direction of desired stretching. Thus, when the incontinence garment is stretched, the consequent unfolding and flattening out of the pleats permits limited but controlled stretching of the primary liquid retention layer in the plane of the garment without distortion of the basic garment shape. The height or depth and the number of the pleats may influence the extent to which the primary liquid retention layer may be stretched.

In another embodiment of the invention, one or more isolated regions of the primary liquid retention layer may be pleated, so as to facilitate stretching only in those regions. In still another embodiment of the primary liquid retention layer, different regions of the absorbent web composite may be provided with pleats oriented in different directions. In each region, the pleats facilitate stretching of the composite in the direction perpendicular to the folds defining the pleats, within the plane of the garment. In still another embodiment, the pleated primary liquid retention layer may be intermittently bonded to a layer of elastic material. By providing an elastic backing, the pleated primary liquid retention layer can be both extended and retracted, the latter occurring when a stretching force is removed.

These and other features and advantages will become further apparent from the following detailed description of the presently preferred embodiments, read in conjunction with the drawings.

DEFINITIONS

The term "nonwoven fabric or web" means a web having a fibrous structure of individual fibers or filaments which are interlaid, but not in an identifiable manner as in a knitted fabric. The terms "fiber" and "filament" are used herein interchangeably. Nonwoven fabrics or webs have been formed from many processes such as, for example, meltblowing processes, spunbonding processes, air laying processes, and bonded carded web processes, etc., and may include cellulosic fibers. The basis weight of nonwoven fabrics is usually expressed in ounces of material per square yard (osy) or grams per square meter (gsm) and the fiber diameters are usually expressed in microns. (Note that to convert from osy to gsm, multiply osy by 33.91.)

The term "microfibers" means small diameter fibers having an average diameter not greater than about 75 microns (μm), for example, having an average diameter of from about 1 micron to about 50 microns, or more particularly, having an average diameter of from about 1 micron to about 30 microns.

The term "spunbonded fibers" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, U.S. Pat. No. 3,502,538 to Petersen, and U.S. Pat. No. 3,542,615 to Dobo et al. Spunbond fibers are quenched and generally not tacky on the surface when they enter the draw unit, or when they are deposited onto a collecting surface. Spunbond fibers are generally continuous and may have average diameters larger than 7 microns, often between about 10 and 30 microns.

The term "meltblown fibers" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than 10 microns in diameter, and are generally self-bonding when deposited onto a collecting surface. Meltblown fibers used in the invention are preferably substantially continuous.

The term "substantially continuous filaments or fibers" refers to filaments or fibers prepared by extrusion from a spinnerette, including without limitation spunbonded and meltblown fibers, which are not cut from their original length prior to being formed into a nonwoven web or fabric. Substantially continuous filaments or fibers may have lengths ranging from greater than about 15 cm to more than one meter; and up to the length of the nonwoven web or fabric being formed. The definition of "substantially continuous filaments or fibers" includes those which are not cut prior to being formed into a nonwoven web or fabric, but which are later cut when the nonwoven web or fabric is cut.

The term "staple filaments or fibers" means filaments or fibers which are natural or which are cut from a manufactured filament prior to forming into a web, and which have a length ranging from about 0.1–15 cm, more commonly about 0.2–7 cm.

The term "fiber" or "fibrous" is meant to refer to a particulate material wherein the length to diameter ratio of such particulate material is greater than about 10. Conversely, a "nonfiber" or "nonfibrous" material is meant to refer to a particulate material wherein the length to diameter ratio of such particulate material is about 10 or less, foam based webs such as cellulosic webs/sponges, and films without significant fiber content.

The terms "elastic" and "elastomeric" are used interchangeably to mean a material that is generally capable of recovering its shape after deformation when the deforming force is removed. Specifically, as used herein, elastic or elastomeric is meant to be that property of any material which upon application of a biasing force, permits that material to be stretchable to a stretched biased length which is at least about 25 percent greater than its relaxed unbiased length, and that will cause the material to recover at least 40 percent of its elongation upon release of the stretching elongating force. A hypothetical example which would satisfy this definition of an elastomeric material would be a one (1) unit length, e.g. centimeter or inch, sample of a material which is elongatable to at least 1.25 units and which, upon being elongated to 1.25 units and released, will recover to a length of not more than 1.15 units. Many elastic materials may be stretched by much more than 25 percent of their relaxed length, and many of these will recover to substantially their original relaxed length upon release of the stretching, elongating force. This latter class of materials is generally beneficial for purposes of the present invention. The term "inelastic" refers to materials that are not elastic.

The term "recover" or "retract" relates to a contraction of a stretched material upon termination of a biasing force following stretching of the material by application of the biasing force.

The term "superabsorbent material" refers to a water swellable, substantially water-insoluble organic or inorganic material capable, under the most favorable conditions, of absorbing at least about 20 times its weight, preferably at least about 30 times its weight in an aqueous solution containing 0.9% by weight sodium chloride. The term "absorbent material" refers to a material which absorbs from about 1 to less than 20 times its weight in an aqueous solution containing 0.9% by weight sodium chloride. INDA Standard Test Method IST 10.1 (95), entitled "Standard Test Method for Absorbency Time, Absorbency Capacity, and Wicking Time," published by INDA, Association of the Nonwoven Fabrics Industry, Cary, N.C., provides the basis for a suitable test method to measure absorbency. The "Absorptive Capacity Test (for small specimens)" may be used to determine the absorbency of a material for the purpose of the subject invention with the following two modifications: (i) IST 10.1 (95) specifies that water is to be used; substitute a 0.9% aqueous sodium chloride solution, (ii) IST 10.1 (95) specifies that a 5 gram sample is used. If necessary, a smaller sample, obtained from an absorbent product may be used instead.

The term "pulp fibers" refers to fibers from natural sources such as woody and non-woody plants. Woody plants include, for example, deciduous and coniferous trees. Non-woody plants include, for instance, cotton, flax, esparto grass, milkweed, straw, jute, hemp, and bagasse. "Cellulosic fibers" maybe naturally occurring, such as pulp fibers, or may be man-made.

The term "incontinence garment" includes without limitation diapers, training pants, and adult incontinence products designed to accept and retain large volumes of voiding liquid from the wearer. A true incontinence garment as used herein in intended to provide at least about 2 g (grams) of liquid retention capacity per $cm^2$ (square centimeter) of retention layer area, and a minimum overall urine (or 0.9% saline) capacity of at least about 200 ml (milliliters).

The term "machine direction" refers to a direction of primary orientation of fibers in a thermoplastic nonwoven web. Following extrusion of nonwoven web filaments, such as spunbond or meltblown filaments, the filaments are typically cooled and carried away on a conveying device or similar apparatus. The machine direction is the direction of primary orientation assumed by the filaments in a nonwoven web, resulting from being drawn and carried away.

The term "transverse direction" refers both to directions perpendicular to the machine direction, and directions within plus or minus 45 degrees of perpendicular to the machine direction within the plane of the material.

Words of degree, such as "about", "substantially", and the like are used herein in the sense of "at, or nearly at, when given the manufacturing and material tolerances inherent in the stated circumstances" and are used to prevent the unscrupulous infringer from unfairly taking advantage of the invention disclosure where exact or absolute figures are stated as an aid to understanding the invention.

"Consisting essentially of" is used in the sense of containing only those elements stated without precluding incidental, insignificant, or nonfunctional amounts of other elements.

DETAILED DESCRIPTION OF THE PRESENTLY PREFERRED EMBODIMENTS

The present invention is directed to a highly absorbent primary liquid retention layer including a combination of nonwoven fibers, a superabsorbent material and, optionally, absorbent fibers. The primary liquid retention layer is pleated in one or more regions thereof, and is stretchable in a direction perpendicular to the folds which define the pleats. The present invention is also directed to an incontinence garment which utilizes the pleated primary liquid retention layer.

Figure 1:
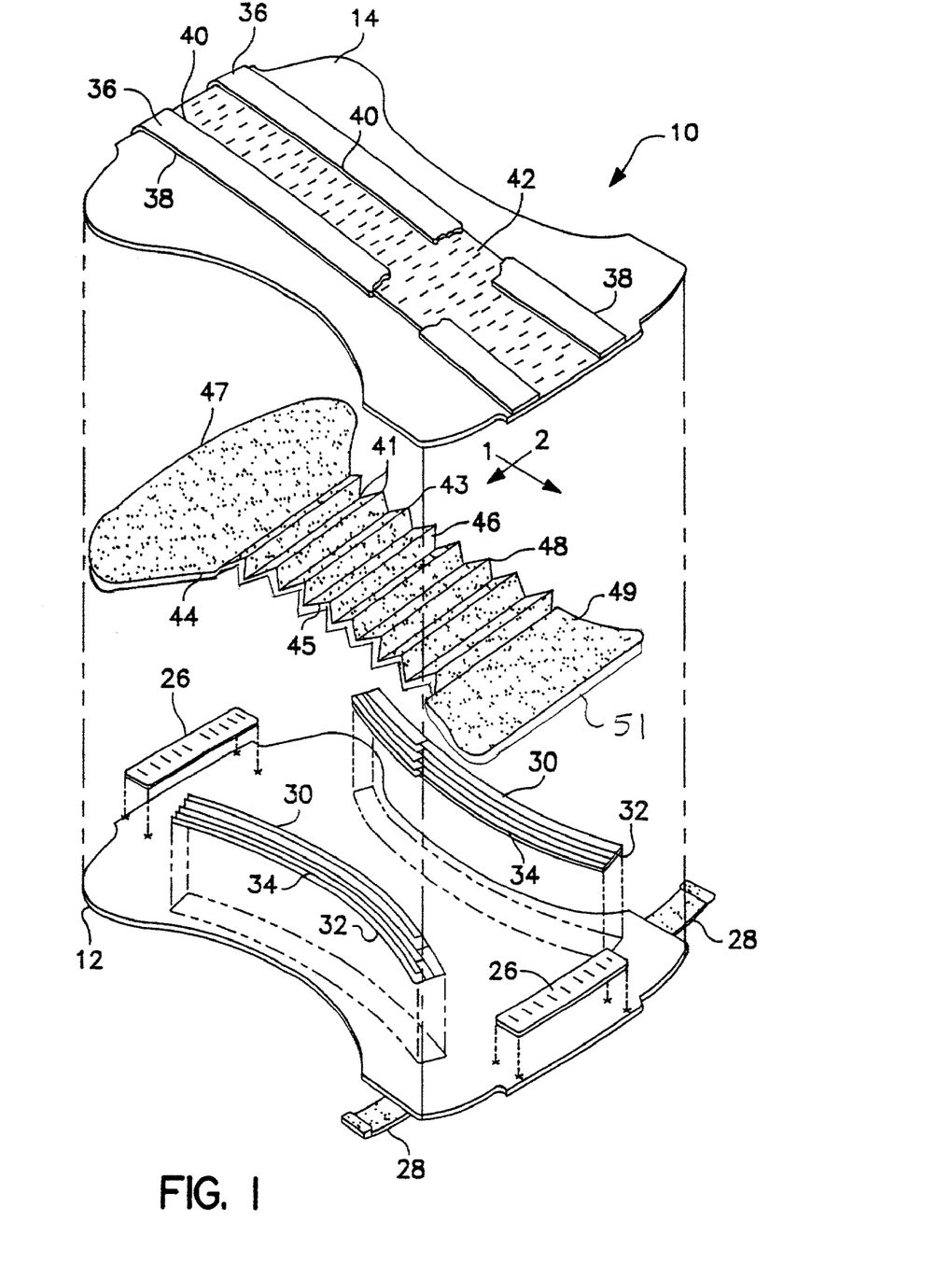
FIG. 1 is an exploded perspective view of one embodiment of an incontinence garment of the invention, in this case, a diaper.

FIG. 1 illustrates an exploded perspective view of a disposable diaper according to one embodiment of the invention. Disposable diaper 10 includes an outer cover 12, a body side liner 14, and a primary liquid retention layer 44 between the outer cover 12 and body side liner 14. Attached to the outer cover 12 are waist elastics 26, fastening tapes 28 and leg elastics 30. The leg elastics 30 include a carrier sheet 32 and individual elastic strands 34. The body side liner includes containment flaps 36 having proximal edges 38 and distal edges 40. A surge management layer 42 is located between the proximal edges 38 of the containment flaps 36.

A possible construction method and materials for a diaper similar to the one illustrated in FIG. 1 are set forth in greater detail in commonly assigned U.S. Pat. No. 5,509,915, issued Apr. 25, 1996 in the name of Hanson et al., incorporated herein by reference. Possible modifications to the diaper illustrated in FIG. 1 are set forth in commonly assigned U.S. Pat. No. 5,509,915 referenced above and in commonly assigned U.S. Pat. No. 5,364,382, issued Nov. 19, 1994 in the name of Matthews et al. Such possible modifications include positioning the surge management layer 42 between the body-side liner 14 and the absorbent primary liquid retention layer 44 and reducing the length of the surge management layer to extend the length of the absorbent composite or massing (reduce length and increase basis weight) the surge management layer in the area of the diaper where liquid waste initially accumulates (target zone).

Figure 2:
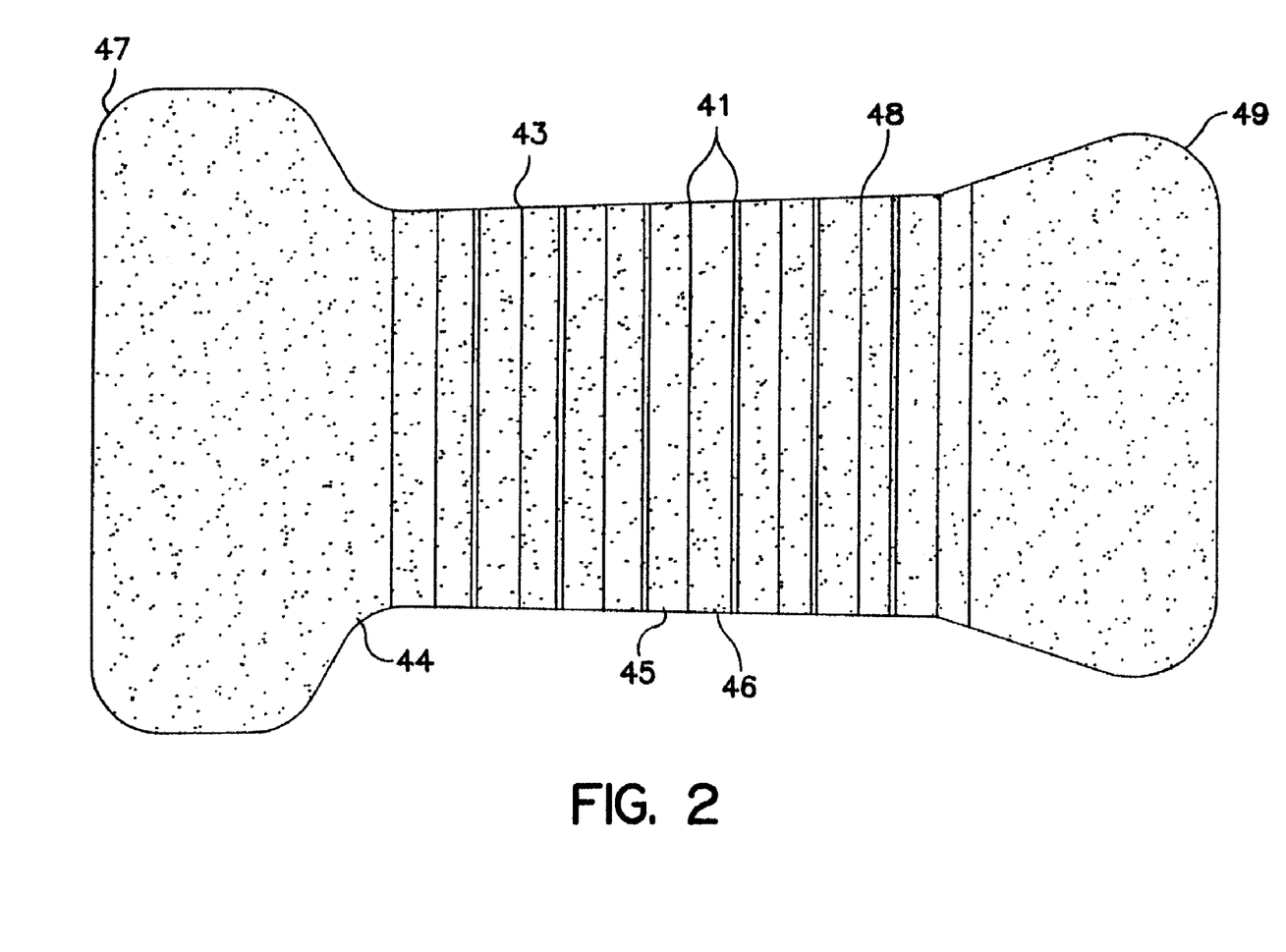
FIG. 2 is a plan view of one embodiment of a pleated primary liquid retention layer of the invention.
Figure 3:
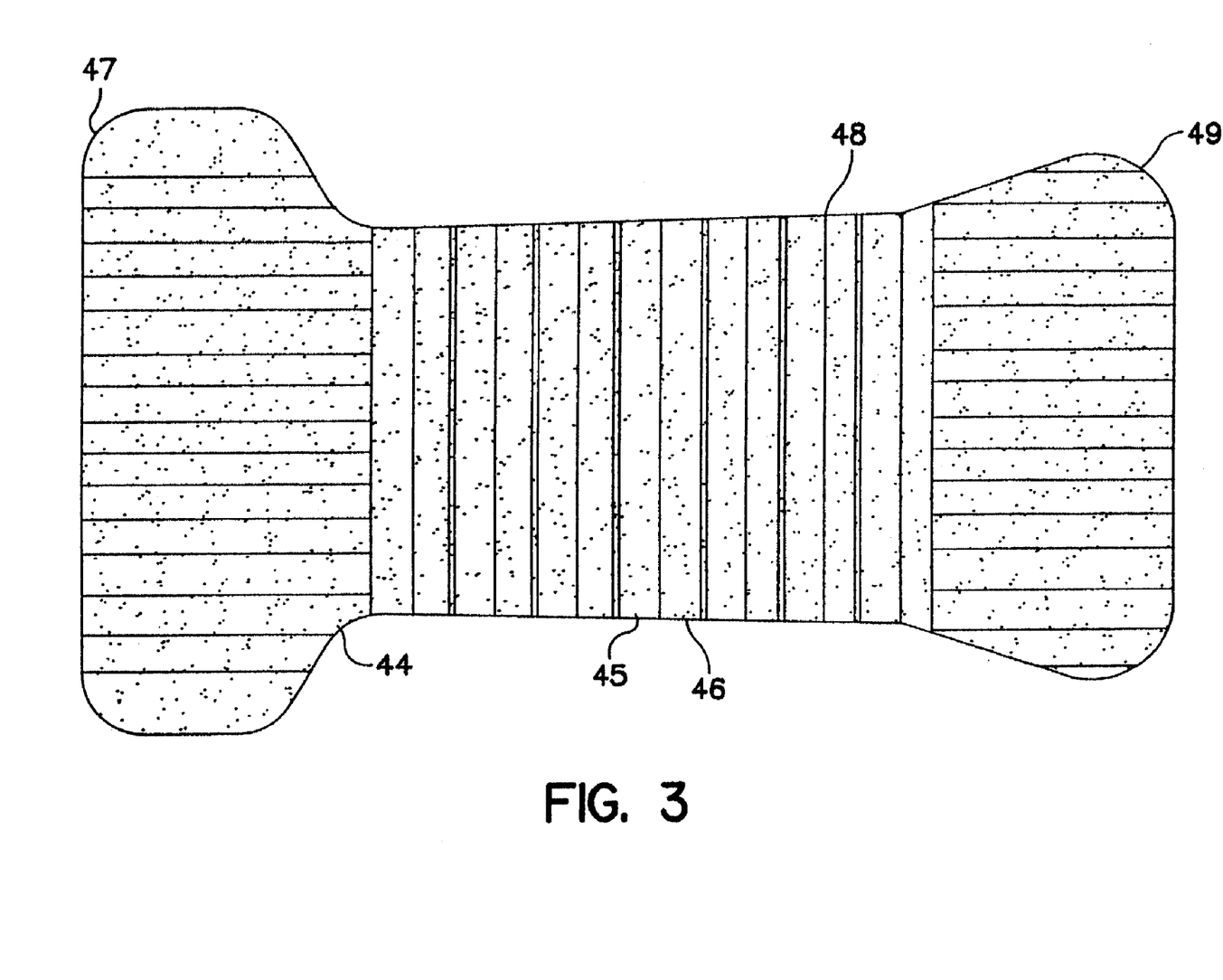
FIG. 3 is a plan view of another embodiment of a pleated primary liquid retention layer of the invention.

FIGS. 2 and 3 illustrate a pleated, fibrous, integrated, primary liquid retention layer 44 in more detail. The primary liquid retention layer 44 may include a single layer in which superabsorbent fibers or particles and, optionally, absorbent fibers are contained among the fibers in a nonwoven fibrous web. Alternatively, the primary liquid retention layer 44 may include multiple layers, for instance, a sandwich structure in which the superabsorbent and optional absorbent fibers are sandwiched between two layers of nonwoven fibrous web.

The primary liquid retention layer 44 should have a basis weight of at least about 200 $g/m^2$ (grams per square meter, or gsm) in order to function as a true incontinence garment which provides at least about 2 g liquid retention capacity per $cm^2$ (square centimeter) of primary liquid retention layer 44 surface area. The primary liquid retention layer 44 should further provide a minimum overall urine capacity of 200 ml (milliliter) for any incontinence garment, including the diaper 10. It is further preferable from an absorbency and retention standpoint that the primary liquid retention layer contain 20% or over superabsorbent material (SAM) by weight of the primary liquid retention layer 44.

Further in order to retain workability, economy, and elasticity while meeting the requisite liquid retention capacities, it is desirable that the primary liquid retention layer have a basis weight of at least 200 $g/m^2$ and no significant foam content.

The illustrated absorbent composite 44 includes a central region 48 in between and adjacent to two end regions 47 and 49. Central region 48 corresponds to the crotch region when the diaper is being worn. End regions 47 and 49 correspond to back and front waist regions when the diaper is being worn. A plurality of pleats 43 are located in central region 48. Each pleat 43 is defined by first and second intersecting surfaces 45 and 46, joined at fold lines 41 representing the apexes of the pleats 43. The fold lines 41 are oriented in a lateral direction 2, which is substantially perpendicular to a longitudinal direction 1, which is the direction of stretching. In most instances, the direction of stretching will correspond to a machine direction defined during manufacture of the composite 44, and the orientation of fold lines 41 will correspond to a cross-machine direction.

The first and second surfaces 45 and 46 are generally of equal area and rectangular, with each surface having a length equal to the width of the primary liquid retention layer 44, and a width equal to the linear distance between the highest point and the lowest point on each pleat 43. This width, which is also referred to as the "surface depth" of the pleats, is an important factor in determining the amount of stretchability of the primary liquid retention layer 44. The surface depth of pleats 43 is equal to the maximum actual depth of pleats 43 when they are folded together like an accordion, and is equal to one-half of the total width of pleats 43 when they are fully extended.

The width or "surface depth" of each rectangular surface 46 varies with the type and size of the incontinence garment, and the amount of stretching required. Generally, the surface depth of pleats 43 (i.e., the shortest linear distance between the highest and lowest points on each pleat) ranges from about 0.1–5 cm, suitably about 0.3–3 cm, desirably about 05.–2 cm. The pleats 43 may be formed using simple folding and pressing techniques.

In the embodiment of FIG. 2, only the central region 48 of primary liquid retention layer 44 is pleated. The pleats permit or enhance longitudinal stretching only in the central region, and do not contribute to stretching in end regions 47 and 49. In the embodiment of FIG. 3, pleats 43 are present in the central and end regions. Pleats 43 in the central region 48 are defined by lateral folds 41, thereby facilitating longitudinal stretching in the central region. Pleats 43 in the end regions 47 and 49 are defined by longitudinal folds, thereby facilitating lateral stretching in the end regions. Other embodiments and pleating configurations are also possible depending on how much stretch is desired, in what direction, and where the stretch is desired.

In one embodiment, the primary liquid retention layer 44 is a unitary or integrated layer which may be a coformed mixture of thermoplastic nonwoven filaments, twenty or more weight percent superabsorbent fibers or particles, and absorbent fibers. In a coformed process, at least one meltblown diehead is arranged near a chute through which other materials are added while the web is forming. Coform processes are described in U.S. Pat. No. 4,818,464 to Lau and U.S. Pat. No. 4,100,324 to Anderson et al., the disclosures of which are incorporated by reference. The thermoplastic nonwoven filaments and absorbent and superabsorbent material may also be combined (i.e., mixed) using hydraulic entangling or mechanical entangling. A hydraulic entangling process is described in U.S. Pat. No. 3,485,706 to Evans, the disclosure of which is incorporated by reference. After combining the ingredients, the absorbent elastic nonwoven composite may be bonded together using the through-air bonding or thermal point bonding techniques described above, to provide a coherent high integrity structure.

Alternatively, the primary liquid retention layer may be formed as a layered structure using two die tips to extrude the nonwoven filaments, and injecting the absorbent and superabsorbent materials as a middle layer between two elastomeric filament layers. Various degrees of mixing of nonwoven filaments and the absorbent/superabsorbent materials can be accomplished to facilitate regions of greater and lesser concentration of elastomeric filaments. This layered structure is an alternative to the absorbent structures produced by a coform process, in which the absorbent ingredients are substantially evenly distributed among individual filaments of an elastomeric nonwoven web.

In still another embodiment, the primary liquid retention layer may include two or more pleated sheets superimposed over one another and joined at the apexes of the pleats 43, as represented by the fold lines 41. Each pleated sheet may be an primary liquid retention layer 44 as described above. Alternatively, when two or more layers are used, the superabsorbent particles or fibers may be contained between the pleated layers, instead of within the pleated layers. The combination of two or more pleated layers may then be extended and retracted like an accordion.

The nonwoven web component(s) of primary liquid retention layer 44 may be a spunbond web, a meltblown web, a bonded carded web, an air laid web, a cellulose or pulp web, or any other microfibrous nonwoven web. Preferably, the nonwoven web is made of thermoplastic polymer fibers. The polymers useful to make the nonwoven web include without limitation polyethylene, polypropylene, copolymers of mainly ethylene and $C_3$–$C_{12}$ alpha-olefins (commonly known as linear low density polyethylene), copolymers of mainly propylene with ethylene and/or $C_4$–$C_{12}$ alpha-olefins, and flexible polyolefins including propylene-based polymers having both atactic and isotactic propylene groups in the main polypropylene chain, and polyamides. Polyesters, including both aromatic and aliphatic polyesters such as poly(lactic acid), may form suitable nonwoven webs. Other suitable polymers include without limitation elastomers, for example polyurethanes, copolyether esters, polyamide polyether block copolymers, ethylene vinyl acetate copolymers, block copolymers having the general formula A-B-A' or A-B such as copoly (styrene/ethylene-butylene), styrene-poly (ethylene-propylene)-styrene, styrene-poly (ethylene-butylene)-styrene, polystyrene/poly(ethylene-butylene)/polystyrene, poly (styrene/ethylene-butylene/styrene), and the like. Metallocene-catalyzed polyolefins are also useful, including those described in U.S. Pat Nos. 5,571,619; 5,322,728; and 5,272,236, the disclosures of which are incorporated herein by reference.

The superabsorbent material used in primary liquid retention layer 44 may be in the form of fibers, particles, or combinations thereof. As explained above, the term "superabsorbent" or "superabsorbent material" refers to a water-swellable, water-insoluble organic or inorganic material capable, under the most favorable conditions, of absorbing at least about 20 times its weight and, more desirably, at least about 30 times its weight in an aqueous solution containing 0.9 weight percent sodium chloride.

The superabsorbent materials can be natural, synthetic and modified natural polymers and materials. In addition, the superabsorbent materials can be inorganic materials, such as silica gels, or organic compounds such as cross-linked polymers. The term "cross-linked" refers to any means for effectively rendering normally water-soluble materials substantially water insoluble but swellable. Such means can include, for example, physical entanglement, crystalline domains, covalent bonds, ionic complexes and associations, hydrophilic associations, such as hydrogen bonding, and hydrophobic associations or Van der Waals forces.

Examples of synthetic superabsorbent material polymers include the alkali metal and ammonium salts of poly(acrylic acid) and poly(methacrylic acid), poly(acrylamides), poly (vinyl ethers), maleic anhydride copolymers with vinyl ethers and alpha-olefins, poly(vinyl pyrrolidone), poly(vinylmorpholinone), poly(vinyl alcohol), and mixtures and copolymers thereof. Further superabsorbent materials include natural and modified natural polymers, such as hydrolyzed acrylonitrile-grafted starch, acrylic acid grafted starch, methyl cellulose, chitosan, carboxymethyl cellulose, hydroxypropyl cellulose, and the natural gums, such as alginates, xanthan gum, locust bean gum and the like. Mixtures of natural and wholly or partially synthetic superabsorbent polymers can also be useful in the present invention. Other suitable absorbent gelling materials are disclosed by Assarsson et al. in U.S. Pat. No. 3,901,236 issued Aug. 26, 1975. Processes for preparing synthetic absorbent gelling polymers are disclosed in U.S. Pat. No. 4,076,663 issued Feb. 28, 1978 to Masuda et al. and U.S. Pat. No. 4,286,082 issued Aug. 25, 1981 to Tsubakimoto et al.

Superabsorbent materials may be xerogels which form hydrogels when wetted. The term "hydrogel," however, has commonly been used to also refer to both the wetted and unwetted forms of the superabsorbent polymer material. The superabsorbent materials can be in many forms such as flakes, powders, particulates, fibers, continuous fibers, networks, solution spun filaments and webs. The particles can be of any desired shape, for example, spiral or semi-spiral, cubic, rod-like, polyhedral, etc. Needles, flakes, fibers, and combinations may also be used.

Superabsorbents are generally available in particle sizes ranging from about 20 to about 1000 microns. Examples of commercially available particulate superabsorbents include SANWET® IM 3900 and SANWET® IM-5000P, available from Hoescht Celanese located in Portsmouth, Va., DRYTECH® 2035LD available from Dow Chemical Co. located in Midland, Mich., and FAVOR® SXM880, available from Stockhausen, located in Greensboro, N.C. An example of a fibrous superabsorbent is OASIS® 101, available from Technical Absorbents, located in Grimsby, United Kingdom.

The optional absorbent fibers used in primary liquid retention layer 44 may be any liquid-absorbing natural or synthetic fibers which are capable, under the most favorable conditions, of absorbing about 1 to less than 20 times their weight in an aqueous solution containing 0.9% by weight sodium chloride. Absorbent fibers include without limitation rayon staple fibers, cotton fibers, natural cellulose fibers such as wood pulp fibers and cotton liners, man-made cellulose fibers, other pulp fibers, and fiberized feathers (e.g., fiberized poultry feathers, such as fiberized chicken feathers.) Pulp fibers are especially useful as the absorbent fibers in the elastomeric nonwoven web composite. Preferred pulp fibers include cellulose pulp fibers, and the like. Other types of absorbent pulp may also be employed.

The primary liquid retention layer 44 may include about 3–80% by weight of the nonwoven web filament matrix, above 20% by weight superabsorbent material, and the remainder by weight of absorbent fibers. Desirably, the primary liquid retention layer 44 includes about 5–50% by weight of the nonwoven web filament matrix, about 25–75% by weight superabsorbent, and about 25–75% by weight absorbent fibers in amounts effective to provide at least 200 ml overall liquid retention capacity and preferably about 2 g liquid retention per square cm of area.

In one embodiment, the pleated primary liquid retention layer 44 may be provided with elastic recovery by laminating the pleated primary liquid retention layer 44 to an elastic sheet 51 when the composite is retracted. When an elastic support sheet is employed, it will stretch when the pleated primary liquid retention layer 44 is extended, and will retract when the stretching force is removed, causing retraction of the pleated primary liquid retention layer 44. The elastic sheet may be a film, nonwoven web, or other material, and is preferably breathable to water vapor. Suitable polymers for making the elastic back sheet include without limitation vulcanized silicone rubber, polyurethane, polyether ester and polyether amide, styrene-butadiene copolymers and terpolymers, elastomeric ethylene-propylene copolymers, and elastomeric single-site or metallocene-catalyzed ethylene polymers and ethylene-alpha olefin copolymers. The primary liquid retention layer 44 may be intermittently bonded to the elastic support layer using a variety of known techniques, including thermal bonding, ultrasonic bonding, adhesive bonding, mechanical stitch bonding, and the like.

In order for the diaper 10 to have overall stretchability similar to the pleated primary liquid retention layer 44, the other layers of the diaper must be at least as stretchable. Both surge layer 42 and body side liner 14 are constructed from highly liquid pervious materials. These layers function to transfer liquid from the wearer to the primary liquid retention layer 44 and to separate the wearer from the primary liquid retention layer 44. Suitable materials include porous woven materials, porous nonwoven materials, and apertured films. Examples include, without limitation, any stretchable porous sheets of polymeric fibers, bonded carded webs of synthetic or natural fibers or combinations thereof. Either layer may also be an apertured stretchable plastic film.

The outer cover 12 may include a single stretchable layer, or may include multiple stretchable layers joined together by adhesive bonding, thermal bonding, ultrasonic bonding or the like. Outer cover 12 can be made from a wide variety of woven or nonwoven material, films, or a film-coated nonwoven material, including, for instance, cast or blown films. Outer cover 12 may also be a composite of a bonded carded or spunbonded or meltblown material, for example, a spunbonded-meltblown composite of thermoplastic material or a spunbonded-meltblown-spunbonded thermoplastic material, wherein the spunbonded layer can provide a cloth-like texture and the meltblown layer can provide liquid impermeability. Outer cover 12 is preferably highly breathable to water vapor.

While the embodiments of the invention disclosed herein are presently considered preferred, various modifications and improvements can be made without departing from the spirit and scope of the invention. The scope of the invention is indicated by the appended claims, and all changes that fall within the meaning and range of equivalency are intended to be embraced therein.

I claim:

1. An incontinence garment, comprising:
    a liquid-permeable body side liner;
    a substantially liquid-impermeable outer cover; and
    a primary liquid retention layer between the body side liner and the outer cover;
    the primary liquid retention layer being folded therethrough to form a plurality of pleats defined by fold lines, the pleats having a folded and an unfolded position;
    wherein each of the pleats comprises two substantially rectangular and equally sized surfaces;
    the primary liquid retention layer being expandable in a direction perpendicular to the fold lines when the pleats absorb liquid; and
    wherein the primary liquid retention layer comprises two layers of nonwoven fibers and superabsorbent material between the layers, the two layers of nonwoven fibers being joined at the fold lines of the pleats so that the primary liquid retention layer may extend and retract along a plane like an accordion.

2. The incontinence garment of claim 1, whereby the primary liquid retention layer expands substantially in the plane of the garment when absorbing liquid.

3. The incontinence garment of claim 1, the primary liquid retention layer providing a liquid absorption capacity of at least 200 ml.

4. The incontinence garment of claim 1, wherein the primary liquid retention layer has a basis weight of at least 200 gsm.

5. The incontinence garment of claim 1, wherein the primary liquid retention layer contains at least 20% by weight superabsorbent material.

6. The incontinence garment of claim 1, wherein the primary liquid retention layer comprises a fibrous web of thermoplastic filaments or cellulose fibers or both.

7. The incontinence garment of claim 1, wherein the pleats have a surface depth of about 0.1–5 cm.

8. The incontinence garment of claim 1, wherein the pleats have a surface depth of about 0.3–3 cm.

9. The incontinence garment of claim 1, wherein the pleats have a surface depth of about 0.5–2 cm.

10. The incontinence garment of claim 1, further including an elastic sheet bonded to the primary liquid retention layer, whereby the primary liquid retention layer may expand and retract.

11. The incontinence garment of claim 1, wherein the primary liquid retention layer comprises a central region and two end regions, with pleats in the central region which are defined by laterally oriented fold lines.

12. The incontinence garment of claim 11, wherein the pleats further comprise pleats in the end regions which are defined by longitudinally oriented fold lines.

13. The incontinence garment of claim 1, wherein the primary liquid retention layer comprises a mixture of thermoplastic nonwoven filaments and superabsorbent particles or fibers.

14. The incontinence garment of claim 1, wherein the layers of nonwoven fibers comprise thermoplastic nonwoven filaments.

15. The incontinence garment of claim 14, further comprising absorbent fibers between the layers of nonwoven fibers.

16. The incontinence garment of claim 1, wherein
a) the primary liquid retention layer expands substantially in the plane of the garment when absorbing liquid;
b) the primary liquid retention layer provides a liquid absorption capacity of at least 200 ml;
c) the primary liquid retention layer has a basis weight of at least 200 gsm, and
d) the primary liquid retention layer contains at least 20% by weight superabsorbent material.

17. The incontinence garment of claim 16, further including an elastic sheet bonded to the primary liquid retention layer.

18. The incontinence garment of claim 16, wherein the primary liquid retention layer comprises a central region and two end regions, with pleats in the central region which are defined by laterally oriented fold lines.

19. The incontinence garment of claim 1 wherein the primary liquid retention layer provides an area absorption capacity of at least 2 gm of liquid per square cm of surface area.

20. An incontinence garment, comprising:
a liquid-permeable body side liner;
a substantially liquid-impermeable outer cover; and
a primary liquid retention layer between the body side liner and the outer cover;
the primary liquid retention layer having a plurality of pleats defined by fold lines, the pleats having a folded and an unfolded position;
wherein each of the pleats comprises two substantially rectangular and equally sized surfaces;
the primary liquid retention layer being expandable in a direction perpendicular to the fold lines when the pleats absorb liquid;
wherein the primary liquid retention layer comprises a central region and two end regions, and pleats in the central region defined by laterally oriented fold lines; and
wherein the primary liquid retention layer comprises two layers of nonwoven fibers and superabsorbent material between the layers, the two layers of nonwoven fibers being joined at the fold lines of the pleats so that the primary liquid retention layer may extend and retract along a plane like an accordion.

21. The incontinence garment of claim 20, wherein the primary liquid retention layer comprises a mixture of thermoplastic nonwoven filaments and superabsorbent particles or fibers.

22. The incontinence garment of claim 20, wherein the layers of nonwoven fibers comprise thermoplastic nonwoven filaments.

23. The incontinence garment of claim 22, further comprising absorbent fibers between the layers of nonwoven fibers.

24. The incontinence garment of claim 20, wherein the primary liquid retention layer further comprises absorbent fibers.

25. The incontinence garment of claim 20, the primary liquid retention layer providing a liquid absorption capacity of at least 200 ml.

26. The incontinence garment of claim 20, wherein the primary liquid retention layer has a basis weight of at least 200 gsm.

27. The incontinence garment of claim 20, wherein the primary liquid retention layer contains at least 20% by weight superabsorbent material.

28. The incontinence garment of claim 20 wherein the primary liquid retention layer provides an area absorption capacity of at least 2 gm of liquid per square cm of surface area.

29. An incontinence garment, comprising:
a liquid-permeable body side liner;
a substantially liquid-impermeable outer cover; and
a primary liquid retention layer between the body side liner and the outer cover;
the primary liquid retention layer having a plurality of pleats defined by fold lines, the pleats having a folded and an unfolded position;
wherein each of the pleats comprises two substantially rectangular and equally sized surfaces;

the primary liquid retention layer being expandable in a direction perpendicular to the fold lines when the pleats absorb liquid; and wherein the primary liquid retention layer provides a liquid absorption capacity of at least 200 ml;

the primary liquid retention layer has a basis weight of at least 200 gsm, and the primary liquid retention layer contains at least 20% by weight superabsorbent material;

the primary liquid retention layer comprises a central region and two end regions, and pleats in the central region defined by laterally oriented fold lines; and wherein the primary liquid retention layer comprises two layers of nonwoven fibers and the superabsorbent material between the layers, the two outer layers of nonwoven fibers being joined at the fold lines of the pleats so that the primary liquid retention layer may extend and retract along a plane like an accordion.

30. The incontinence garment of claim 29, wherein the primary liquid retention layer comprises a mixture of thermoplastic nonwoven filaments and superabsorbent particles or fibers.

31. The incontinence garment of claim 30, wherein the primary liquid retention layer further comprises absorbent fibers.

32. The incontinence garment of claim 29 wherein the primary liquid retention layer provides an area absorption capacity of at least 2 gm of liquid per square cm of surface area.

* * * * *